United States Patent
Heikenfeld et al.

(10) Patent No.: US 12,259,352 B2
(45) Date of Patent: Mar. 25, 2025

(54) MEMBRANE ENHANCED SENSORS

(71) Applicant: University Of Cincinnati, Cincinnati, OH (US)

(72) Inventors: Jason Charles Heikenfeld, Cincinnati, OH (US); Yuchan Yuan, Cincinnati, OH (US); Madeleine Debrosse, Cincinnati, OH (US); Michael Charles Brothers, Lebanon, OH (US)

(73) Assignee: University of Cincinnati, Cincinnati, OH (US)

( * ) Notice: Subject to any disclaimer, the term of this patent is extended or adjusted under 35 U.S.C. 154(b) by 1025 days.

(21) Appl. No.: 17/053,007

(22) PCT Filed: May 3, 2019

(86) PCT No.: PCT/US2019/030599
§ 371 (c)(1),
(2) Date: Nov. 4, 2020

(87) PCT Pub. No.: WO2019/213520
PCT Pub. Date: Nov. 7, 2019

(65) Prior Publication Data
US 2021/0364464 A1    Nov. 25, 2021

Related U.S. Application Data

(60) Provisional application No. 62/666,921, filed on May 4, 2018.

(51) Int. Cl.
| | |
|---|---|
| *G01N 27/333* | (2006.01) |
| *A61B 5/145* | (2006.01) |
| *A61B 5/1468* | (2006.01) |
| *G01N 1/40* | (2006.01) |
| *G01N 21/01* | (2006.01) |

(52) U.S. Cl.
CPC ....... *G01N 27/333* (2013.01); *A61B 5/14517* (2013.01); *A61B 5/1468* (2013.01); *G01N 1/4005* (2013.01); *G01N 21/01* (2013.01)

(58) Field of Classification Search
CPC ...... G01N 27/333; A61B 5/145; A61B 5/1468
See application file for complete search history.

(56) References Cited

U.S. PATENT DOCUMENTS

| | | | | |
|---|---|---|---|---|
| 3,632,483 | A | * | 1/1972 | Baum ................ G01N 27/3335 564/8 |
| 4,479,865 | A | * | 10/1984 | Beder .................... G01N 27/28 204/415 |
| 2004/0182707 | A1 | * | 9/2004 | Jardemark ............. B82Y 15/00 204/601 |
| 2017/0097348 | A1 | | 4/2017 | Mehrpouyan | |

FOREIGN PATENT DOCUMENTS

| | | |
|---|---|---|
| EP | 3054290 A1 | 8/2016 |
| WO | 2018006087 A1 | 1/2018 |

OTHER PUBLICATIONS

Extended European Seach Report in European Patent Application No. 23207000.3, dated Feb. 16, 2024, 8 pgs.
Helwa, Youssef et al: "Aptamer-Functionalized Hydrogel Microparticles for Fast Visual Detection of Mercury(II) and Adenosine", Applied Materials & Interfaces, vol. 4, No. 4, Apr. 9, 2012 (Apr. 9, 2012), pp. 2228-2233.
Zhen, Li et al: "Aptamer-functionalized porous phospholipid nanoshells for direct measurement of Hg2+in urine", Analytical and Bioanalytical Chemistry, Springer Berlin Heidelberg, Berlin/Heidelberg, vol. 407, No. 3, Oct. 19, 2014, pp. 953-960.
International Search Authority, Search Report and Written Opinion issued in corresponding PCT Application No. PCT/US2019/030599, mailing date Aug. 1, 2019, pages.

* cited by examiner

*Primary Examiner* — Randy Boyer
(74) *Attorney, Agent, or Firm* — Wood Herron & Evans LLP

(57) ABSTRACT

A sensing device for detecting a characteristic of an analyte in a sample solution and method of making the same is provided. The device includes one or more sensors configured to measure a characteristic of an analyte in a sample. The device further includes a sample solution that contains the analyte and one or more interfering solutes, wherein the interfering solute reduces a performance characteristic of the one or more sensors. The device further includes a sensor solution in fluidic communication with the one or more sensors. The device further includes a hydrophobic barrier that separates the sample solution from the one or more sensors, wherein the hydrophobic barrier is permeable to the analyte and impermeable to the interfering solute, and wherein the hydrophobic barrier is in fluidic communication with the sample solution and the sensor solution.

36 Claims, 3 Drawing Sheets

MEMBRANE ENHANCED SENSORS

CROSS-REFERENCE TO RELATED APPLICATIONS

This application is a U.S. National Phase Application and claims benefit of and priority to PCT Application No. PCT/US2019/030599 filed May 3, 2019, which in turn claims the benefit of U.S. Provisional Application No. 62/666,921, filed May 4, 2018. The disclosures of the aforementioned applications are incorporated herein by reference in their entireties.

STATEMENT REGARDING FEDERALLY SPONSORED RESEARCH OR DEVELOPMENT

This invention was made with government support under government funding number F4FBRE6098G001 awarded by the Oak Ride Institute for Science and Education (ORISE), an institute of the United States Department of Energy. This invention was made with further government support under contract number FA8650-14-D-6516 awarded by the Air Force Research Laboratory, Human Performance Wing, an organization operated by the United States Air Force. The government has certain rights in the invention.

BACKGROUND OF THE INVENTION

Monitoring analytes using sensors is an attractive modality for chemical sensing and biosensing, but sensors can struggle to achieve low limits of detection for small analytes, particularly for small analytes that are not chemically diverse in their structure (e.g., uniformly hydrophobic or uniformly hydrophilic). This can be especially true for sensors that are immersed in a liquid sample, such a biofluid or environmental water, a sample which may contain not only an analyte of interest, but also many other compounds that can create background noise or reduce the sensitivity of the sensor for the analyte of interest. For example, for electrochemical enzymatic sensors and aptamer sensors, a large amount of other solutes in biofluid samples are redox active and increase the background electrical current or noise. Moreover, the sample may contain components, such as ions, that interfere with the operation of the analyte sensor. For example, potential of hydrogen (pH), salinity, and other variable biofluid or environmental factors can cause changes in sensor signal that are greater than the changes caused by the target analyte. Furthermore, solutes and/or solvents can also degrade the sensor, for example, by degrading aptamer probe chemistry. New techniques are needed that can leverage sensor technology to allow for detection of small molecules and hydrophobic analytes in complex liquid samples.

SUMMARY OF THE INVENTION

In various embodiments of the disclosed invention, a hydrophobic barrier can be used to separate a sensor from a sample solution, such as a biofluid or environmental fluid, allowing the analyte of interest to reach the sensor while preventing hydrophilic species in the sample, such as pH, salt, or redox active molecules from reaching and degrading the sensor.

BRIEF DESCRIPTION OF THE DRAWINGS

The objects and advantages of the disclosed invention will be further appreciated in light of the following detailed descriptions and drawings in which.

DEFINITIONS

Figure 1A:
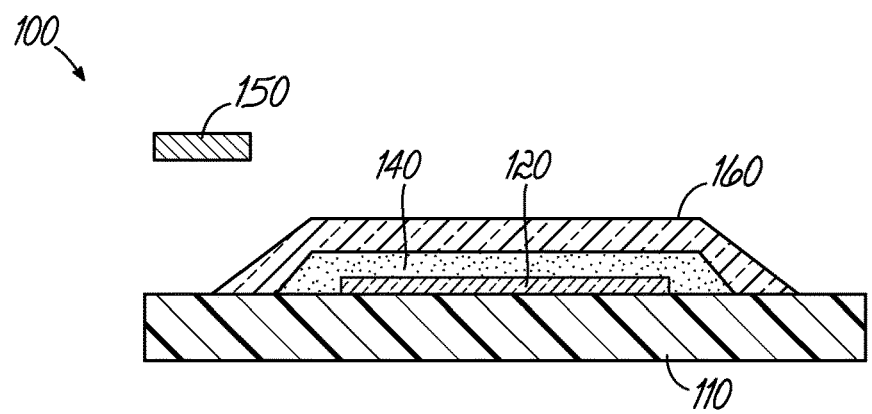
FIG. 1A is a cross-sectional view of at least a portion of a membrane enhanced sensor of the disclosed invention.

As used herein, "continuous sensor" or "continuous sensing" means the capability of a device to provide a plurality of measurements over time by continuous or repeated collection and sensing of a property of a sample fluid.

As used herein, "reversible sensor" means the sensor is configured to measure both increasing and decreasing concentrations of an analyte in sample fluid without any additional change in the sensor's stimulus or environment other than changes in analyte concentration.

As used herein, "analyte specific sensor" is any sensor (chemical, electrical, optical, mechanical, etc.) for continuous monitoring that is able to selectively and sensitively measure at least one analyte in a fluid sample.

As used herein, an "interfering solute" is a solute in a sample solution that significantly interferes with sensing of a target analyte and/or degrades an analyte specific sensor.

As used herein, "hydrophobic barrier" refers to materials through which non-charged, non-hydrophilic, or hydrophobic solutes will diffuse, but through which charged or hydrophilic solutes that interfere with a sensor will not diffuse. For example, hydrocarbons or vegetable oils can allow a hydrophobic analyte such as ethanol, cortisol, or acetaminophen to diffuse through them, but can block ions such as $Ca^+$, $K^+$, $Na^+$ and $Cl^-$ and $OH^-$, $H^+$, or lactic acid (e.g., block pH-altering solutes). More simply stated, the hydrophobic solutes, even though potentially larger in size, diffuse more rapidly through hydrophobic material. Hydrophobic barriers may also be semi-solid or solid, such as layers of hydrocarbon, silicone greases, or polymers. A hydrophobic barrier may also be defined as a material with a permeability coefficient (cm/s) for at least one interfering solute that significantly interferes with sensing of the analyte and/or degrades the sensor, where the permeability coefficient for the at least one solute is at least one of the following: greater than (>) 10×, >100× or >1000× lower than the permeability coefficient for at least one target analyte. Non-limiting target analyte examples include ethanol, cortisol, acetaminophen, or cyclosporin A. The hydrophobic barrier provides the selective permeability properties specified above for at least one hydrophobic analyte, and at least one hydrophilic interfering solute. By contrast, there may be solutes that pass through the hydrophobic barrier that are hydrophilic and/or charged, but which do not significantly interfere with the sensor and/or degrade the sensor. A hydrophobic barrier as defined herein is not simply a size-selective membrane.

As used herein, "sensor solution" refers to materials through which an analyte will diffuse and in which a sensor is bathed, contained, or which partially forms the sensor. For example, an electrochemical aptamer sensor could be bathed in a sensor solution containing a pH buffer, a salt, and a preservative. As another example, instead of being bathed in a solution, a sensor may be combined with a molecular-imprinted polymer that contains within its porous network a sensor solution with a pH buffer and/or salt solutes.

As used herein, "sample solution" refers to any liquid or fluid which contains at least one analyte that is to be measured in presence, change, concentration, or other measurement, by a sensor specific to that analyte. A sample or sample solution may be a biofluid, but could also be water from the environment, manufacturing fluid for food, or other types of sample solutions that would benefit from the disclosed invention.

As used herein, "biofluid" means a fluid source of analytes originating in the human body. For example, sweat is a biofluid source of analytes that is from eccrine or apocrine glands. For another example, a biofluid could be a solution that bathes and surrounds tissue cells such as interstitial fluid. Embodiments of the disclosed invention may focus on interstitial fluid found in the skin extracted through microneedles and, particularly, interstitial fluid found in the dermis. Biofluid could also include blood, saliva, tears, or other possible biofluids.

DETAILED DESCRIPTION OF THE INVENTION

Embodiments of the disclosed invention apply to sensor devices and methods for measuring analyte concentrations. Further, embodiments of the disclosed invention may apply to sensing devices, which can take on forms including cassettes, cartridges, patches, bands, straps, portions of clothing, wearables, or any suitable mechanism that reliably brings sensing technology into proximity with a biofluid containing a target analyte.

Sweat stimulation, or sweat activation, can be achieved by known methods. For example, sweat stimulation can be achieved by simple thermal stimulation, chemical heating pad, infrared light, by orally administering a drug, by intradermal injection of drugs such as carbachol, methylcholine or pilocarpine, and by dermal introduction of such drugs using iontophoresis, by sudo-motor-axon reflex sweating, or by other means. A device for iontophoresis may, for example, provide direct current and use large lead electrodes lined with porous material, where the positive pole is dampened with 2% pilocarpine hydrochloride or carbachol and the negative one with 0.9% NaCl solution. Sweat can also be controlled or created by asking the device wearer to conduct or increase activities or conditions that cause them to sweat.

One skilled in the art will recognize that the various embodiments may be practiced without one or more of the specific details described herein, or with other replacement and/or additional methods, materials, or components. In other instances, well-known structures, materials, or operations are not shown or described in detail herein to avoid obscuring aspects of various embodiments of the invention. Similarly, for purposes of explanation, specific numbers, materials, and configurations are set forth herein in order to provide a thorough understanding of the invention. Furthermore, it is understood that the various embodiments shown in the figures are illustrative representations and are not necessarily drawn to scale.

Reference throughout this specification to "one embodiment" or "an embodiment" means that a particular feature, structure, material, or characteristic described in connection with the embodiment is included in at least one embodiment of the invention, but does not denote that they are present in every embodiment. Thus, the appearances of the phrases "in an embodiment" or "in another embodiment" in various places throughout this specification are not necessarily referring to the same embodiment of the invention. Further, "a component" may be representative of one or more components and, thus, may be used herein to mean "at least one."

Certain embodiments of the invention show sensors as simple individual components. It is understood that many sensors require two or more electrodes, reference electrodes, or additional supporting technology or features that are not captured in the description herein. Sensors are preferably electrical in nature, but may also include optical, chemical, mechanical, or other known biosensing mechanisms. Sensors can be in duplicate, triplicate, or more, to provide improved data and readings. Sensors may be referred to by what the sensor is sensing, for example: a sweat sensor; an impedance sensor; a fluid volume sensor; a sweat generation rate sensor; and a solute generation rate sensor. Certain embodiments of the disclosed invention show sub-components of what would be fluid sensing devices with more sub-components needed for use of the device in various applications, which are obvious (such as a battery), and for purpose of brevity and focus on inventive aspects are not explicitly shown in the diagrams or described in the embodiments of the invention. As a further example, many embodiments of the invention could benefit from mechanical or other means known to those skilled in wearable devices, patches, bandages, and other technologies or materials affixed to skin, to keep the devices or sub-components of the skin firmly affixed to skin or with pressure favoring constant contact with skin or conformal contact with even ridges or grooves in skin, and are included within the spirit of the disclosed invention.

The disclosed sweat sensing device also includes computing and data storage capability sufficient to operate the device, which incorporates the ability to conduct communication among system components, to perform data aggregation, and to execute algorithms capable of generating notification messages. The device may have varying degrees of onboard computing capability (i.e., processing and data storage capacity). For example, all computing resources could be located onboard the device, or some computing resources could be located on a disposable portion of the device and additional processing capability located on a reusable portion of the device. Alternatively, the device may rely on portable, fixed or cloud-based computing resources.

Figure 1B:
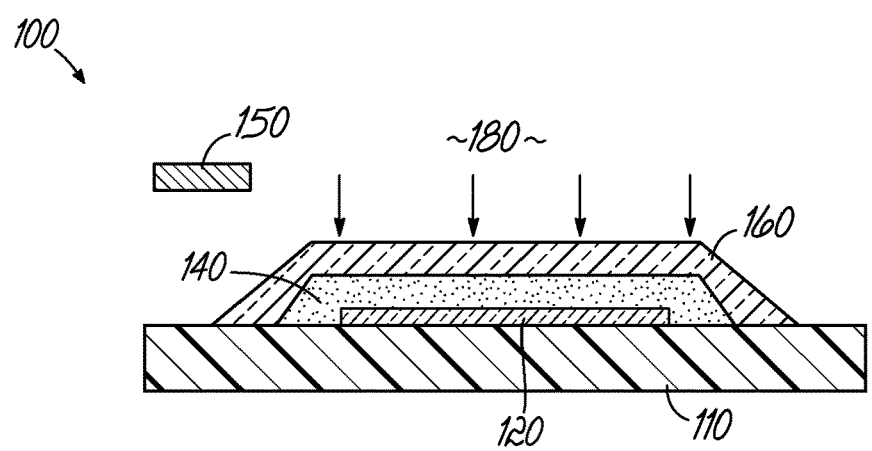
FIG. 1B is another cross-sectional view of at least a portion of a sensor of the disclosed invention.

With reference to FIG. 1A, a device 100 includes a substrate 110, an analyte specific sensor 120, a sensor solution 140, a hydrophobic barrier 160, and an electrode 150. The device may be placed into or adjacent to a sample solution 180 as shown in FIG. 1B. The substrate 110 is any material suitable for supporting the sensor 120 and is typically a solid and inert material. Exemplary substrates 110 may be comprised of glass or PET. Electrode 150, may be for example, a counter electrode of silver, silver chloride, gold, carbon, poly(3,4-ethylenedioxythiophene) (PEDOT), or other materials suitable to function as an electrode.

At least one analyte specific sensor 120 is capable of detecting a molecule of interest and may be optical, mechanical, electronic or other suitable means of sensing. For example, in various embodiments, the sensor 120 may include an electrochemical sensor such as an enzymatic sensor, an aptamer with a redox tag, an impedimetric sensor, a molecular imprinted polymer sensor, or other types of sensors. In some examples, the sensor 120 is directly coupled to the substrate 110. Sensor 120 may be a continuous sensor, or a continuous and reversible sensor, e.g., an electrochemical aptamer sensor as disclosed in U.S. Pat. Nos. 7,803,542, and 8,003,374. Example analytes may include, but are not limited to, steroid hormones e.g., cortisol, estrogen, molecular drugs, e.g., acetaminophen, warfarin, or peptides, e.g., cyclosporin A, transactivator of transcription (TAT).

Sensor solution 140 is configured to support diffusion of the target analyte into fluidic communication with the sensor, and support reliable operation of the sensor 120. For example, the solvent in the sensor solution 140 could be water, a glycol, an alcohol, an ionic liquid, an oil, or other suitable liquid or fluid. The solvent may contain solutes. For example, an aqueous solvent could contain sucrose, a redox moiety, e.g., methylene blue, a salt, e.g., potassium chloride, a buffer, e.g., citrate or 10 mM tris(hydroxymethyl)aminomethane (Tris) and HCl to bring pH to 8.0, a preservative, or any combination thereof, or one or more different solutes or solute types. For example, the pH of sensor solution 140 could be controlled in the solvent such that the pH is always greater than 7, or near 7. Alternatively, the salt concentration can be controlled so that a chloride ion content of the sensor solution is always greater than 10 mM. Therefore, the sensor solution may include at least one salt, at least one buffering solute, or at least one other solute, such as preservative.

Hydrophobic barrier 160 is able to pass at least one target analyte to at least one sensor 120 specific to the target analyte, and is able to block at least one interfering solute in a sample solution 150. The hydrophobic barrier 160 is a material that has a permeability coefficient (cm/s) for at least one interfering solute, where the permeability coefficient for the at least one interfering solute is at least one of less than one tenth, less than one hundredth, or less than one thousandth of the permeability coefficient for at least one target analyte.

For example, hydrophobic barrier 160 could be layers of hydrocarbons or vegetable oils that allow a hydrophobic analyte to diffuse through them, but block ions, such as $Ca^+$, $K^+$, $Na^+$, $Cl^-$, $OH^-$, $H^+$, or lactic acid (i.e., the barrier can block pH-altering solutes). Hydrophobic barriers may also be semi-solid or solid, such as silicone greases or polymers. Each target analyte may have a different hydrophobic barrier that is ideal for that target analyte or device application, which may be characterized in terms of properties such as surface tension, solubility limits, $\log_{10}$(Partition Coefficient) (logP), thickness, porosity, solutes, surfactants, a plurality of miscible or immiscible hydrophobic materials, lag times, etc. In general, a well-designed or ideal hydrophobic barrier 160 for a particular target analyte will have properties that 1) facilitate analyte partitioning from the sample solution 180 into the barrier; e.g., by reducing the required time and/or energy; 2) facilitate analyte diffusion through the hydrophobic barrier, e.g., by reducing the required time and/or the viscosity of an oil or fluid in the hydrophobic barrier which can hinder the velocity of diffusion of the analyte; and 3) facilitate analyte partitioning from the hydrophobic barrier into the sensor solution 140 and to the sensor, e.g., by reducing the required time and/or energy. Furthermore, for aptamer based and other reversible sensors, the hydrophobic barrier must fully and quickly allow the analyte to leave the sensor and return to the sample solution 180.

With further reference to FIG. 1, although hydrophobic barriers 160 may be comprised of solid or semi-solid materials (polymers, greases, etc.), in some embodiments, the hydrophobic barrier 160 may be comprised of a fluid supported by a solid scaffold. For example, a hydrophobic track-etch membrane could have its pores impregnated with castor oil, thus forming a suitable hydrophobic barrier (see Examples below). Furthermore, the hydrophobic barrier as described may possess properties as outlined for the materials listed in Table 1, but is not so limited for all possible embodiments. Specific terms used herein such as fluids or oils do not limit the embodiments of the present invention. For example, oil is used for convenience and is used in its broadest meaning, e.g., a fluid that immiscible with water or other polar fluids.

TABLE 1

| | Melting Point | logP | Solubility in Water | Boiling Point | Vapor Pressure | Carbons | Double Bonds (in chain) | Surface Tension |
|---|---|---|---|---|---|---|---|---|
| Oleic Acid | 61.3° F. | 7.64 | 10 μg/L | 547° F. | 0.0000005 mmHg | 18 | 1 | |
| Linoleic Acid | 23° F. | 6.8 | 1.59 mg/L | 445° F. | 0.00000087 mmHg | 18 | 3 | |
| Palmitoleic Acid | 32° F. | 6.4 | Low | 285° F. | 0.000067 to 1.7 mmHg | 16 | 1 | |
| Arachidonic Acid | −50° C. | 7 | Negligible | High | ~0 mmHg | 20 | 4 | |
| Decanol | 44° F. | 4.57 | 30 mg/L | 446° F. | 0.00851 mm Hg | 10 | 0 | |
| Castor Oil | −10 to −12° C. | 17.72 | <0.001 mg/mL | 313° C. | ~0 mmHg | 57 | 3 | |
| Tetradecane | 6° C. | 8.19 | 0.00091 to 0.0022 mg/L | 253° C. | 0.0369 mmHg | 14 | 0 | |
| Mesitylene | 45° C. | 3.4 | 0.0482 mg/mL | 163-166° C. | 2 mmHg | 9 | 3 | |
| Ricinoleic Acid | 5.5° C. | 5.7 | 3460 mg/L | 245° C. | ~0 mmHg | 18 | 1 | |
| 10-Thiasteric Acid | | | | | | 21 | 6 | |
| Eicosenoic Acid | 23° C. | 8.76 | 0.00096 to 0.0019 mg/L | | ~0 mmHg | 20 | 1 | |
| Phytanic Acid | | 8.3 | 0.002 to 0.0068277 mg/L | 7.5° C.? | ~0 mmHg | 20 | 0 | |
| Myristoleic Acid | | 5.1 | 0.94 to 2.3128 mg/L | | ~0 mmHg | 14 | 1 | |
| Parinaric Acid | | 5.9 | ? | | ~0 mmHg | 18 | 4 | |
| 2-Linoleoyl Glycerol | | 5.6 | 0.030 to 0.56 mg/L | | ~0 mmHg | 21 | 2 | |
| Myristelaidic Acid | | 5.1 | 0.002 g/L | | ~0 mmHg | 14 | 1 | |

TABLE 1-continued

| | Melting Point | logP | Solubility in Water | Boiling Point | Vapor Pressure | Carbons | Double Bonds (in chain) | Surface Tension |
|---|---|---|---|---|---|---|---|---|
| Anacardic Acid | 93° C. | 9.5 | ~0.0005914 mg/L | | ~0 mmHg | 22 | 3 | |

With reference to Table 1 and embodiments of the disclosed invention, although logP is typically used to characterize fluids, logP is used here more broadly to interpret the effectiveness of a hydrophobic barrier, even if the hydrophobic barrier is not a liquid, is multilayered, multi-materialled, or some other deviation from a simple fluid. logP is the partition coefficient for an oil between 1-octanol and water, it is useful for rapidly screening the relative hydrophobicity and/or hydrophilicity of fluid with respect to an analyte or solute. With further reference to Table 1, logP values listed are for water/octanol. The disclosed invention may benefit from a hydrophobic barrier with a logP that is at least one of greater than −3, greater than −1, greater than 1, greater than 3, or greater than 5. Not shown in Table 1, logP can also be measured with respect to analyte concentrations found in the sample solution 180, sensor solution 140, or hydrophobic barrier 160, referenced herein as "analyte logP". To maximize speed of transport for an analyte into and out of the device 100, the analyte logP will be between at least one of −1 and 1, −3 and 3, and −5 and 5.

Using logP to interpret the effectiveness of a hydrophobic barrier, consider an oil fluid having a water solubility of 50 mg/100 g (50 μg/g) as the hydrophobic barrier. If this oil fluid were embedded in a membrane that is 10% porous by volume and 10 μm thick, then the effective thickness of the oil fluid is ~1 μm. Next, assume a 10 μm thick sample solution adjacent to the oil fluid that is flowed over the entire device (e.g., a continuous sweat biosensing device) so that new sample fluid is brought to the sensor every 10 minutes. Fresh sample fluid could then be brought to the sensor a total of 0.1*100/50E-3=200 times before the oil fluid is depleted (i.e., dissolved fully into the sample solution). The device would therefore last 33.3 hours before the oil fluid is depleted. The disclosed invention may therefore include a hydrophobic barrier at least partially comprised of a fluid with solubility limits in the sample solution that are at least one of less than 500 micrograms of fluid per gram of sample solution, less than 50 micrograms of fluid per gram of sample solution, less than 5 micrograms of fluid per gram of sample solution, or less than 0.5 micrograms of fluid per gram of sample solution, resulting in hydrophobic barrier lifetimes of at least one of greater than 3 hours, greater than 30 hours, greater than 300 hours, or greater than 3000 hours.

With further reference to Table 1, and FIGS. 1A and 1B, hydrophobic barrier 160 thickness will influence device operation. If the hydrophobic barrier is too thick, it can behave as a sink or storage location for the target analyte, and may lengthen the diffusive pathway the target analyte must traverse to reach the sensor 120. Therefore, hydrophobic barrier thickness may be at least one of less than 1 millimeter, less than 100 micrometers, less than 10 micrometers, less than 1 micrometer, or less than 0.1 micrometers.

With further reference to Table 1, and FIGS. 1A and 1B, hydrophobic barrier 160 porosity will influence operation of the device 100. For example, a Teflon membrane or track etch membrane may be used as a solid scaffold to support an oil fluid, creating the hydrophobic barrier. If the porosity is low, target analyte diffusion and transport will be limited. Therefore, the hydrophobic barrier may have a porosity that is at least one of greater than 0.1%, greater than 1%, greater than 10%, or greater than 30%.

With reference to Table 1 and FIGS. 1A and 1B, sensor solution 140 thickness will influence proper device 100 operation. The greater the thickness of the sensor solution, the longer the diffusive pathway to the sensor 120, and the larger the volume that must be equilibrated with analyte concentration in the sample solution 180. Sensor solution thickness therefore is at least one of less than 3 millimeters, less than 1 millimeter, less than 300 micrometers, less than 100 micrometers, less than 30 micrometers, or less than 10 micrometers.

With reference to Table 1, FIGS. 1 and 1B, as well as the Examples below, the device 100 will exhibit a concentration lag time that represents the time required for a concentration change in the sensor solution 140 to reach 90% of the concentration in the sample solution 180. Given cortisol as the target analyte, a sensor solution with a thickness of hundreds of micrometers, and a hydrophobic barrier 160 comprising a track-etch membrane of 10% porosity filled with castor oil, the concentration lag time can be on the order of 30 minutes. Optimizing the parameters above (logP, oil choice, thicknesses, etc.) results in concentration lag times that are at least one of less than 300 minutes, less than 100 minutes, less than 30 minutes, less than 10 minutes, less than 3 minutes, or less than 1 minute.

With reference to Table 1, and FIGS. 1A and 1B, two or more oils may be blended in miscible form to obtain an oil fluid with optimal properties as outlined above, but not so limited to the specific oils or properties listed above. For example, additional properties may include a wider operating temperature range for an oil blend, i.e. those found in phospholipid membranes with varying chain fatty acids, degrees of fatty acid chain unsaturation, as well as cholesterol provides favorable mechanical and chemical properties. A third oil or plurality of oils may also be used to obtain the desired set of properties. Therefore, embodiments of the invention may include a hydrophobic barrier 160 that is at least partially comprised of a plurality of miscible oils. Oils may also be immiscible, for example a 10 μm track etch membrane is filled with a first oil that is partially evaporated to form 2 μm thick plugs, then a second oil is added on one or both sides of the first oil plugs to form a hydrophobic barrier that is at least partially comprised of a plurality of immiscible oils. As configured, multiple immiscible oils may provide superior blocking of hydrophilic solute compared to a single oil (e.g., one oil may be better at blocking one type of hydrophilic solutes than the other). Furthermore, this may allow for more energy-favorable stepping of analyte transport (e.g., Oil 1: logP=2, Oil 2: logP=4, then Oil 3: logP=2, which is more favorable than directly bridging the energy gap created by a single oil with logP=4). Oil or fluids inside the hydrophobic membrane 160 may also incorporate at least one solute that alter their logP values or some other property, and/or may include at least one surfactant which aids transport into or out of the oil fluid. For example, one or more phospholipids could effect the oil as a solute and/or as a surfactant. Other examples of oils or fluids may include chlorinated or fluorinated solvents (that are oleophobic) and aromatic solvents (i.e. xylenes). Furthermore, this may allow for removal of interfering compounds through multi-phase selection (i.e. a compound that has a partition coefficient >0.001 into both xylene and trichloroethylene versus an interferant which has a partition coefficient of <0.001 for one or both oils).

With further reference to Table 1, and FIGS. 1A and 1B, the present invention may include a hydrophobic barrier 160 that includes an oil that has a low vapor pressure such that the shelf life of the device (to the extent set by oil evaporation rates at a room temperature of 72° F., +/−5° F.) is at least one of greater than 24 hours, greater than 1 week, greater than 1 month, or greater than 1 year.

With reference to Table 1, and FIGS. 1A and 1B, the disclosed invention may include a hydrophobic barrier 160 that contains an oil with a low viscosity to allow an analyte to rapidly diffuse through the oil. Because of this relative ease of analyte diffusion, lower viscosities are desired. Therefore fluid for use in the hydrophobic barrier has a viscosity that is at least one of less than 1000 centipoise, less than 100 centipoise, or less than 10 centipoise. Example hydrophobic barrier oils include castor oil (viscosity of 650 centipoise (cP)) and dodecane (viscosity of 1.4 cP).

With further reference to FIG. 1, and FIGS. 1A and 1B, analytes that are ionized by factors such as pH in the sample solution 180 or sensor solution 140 will have greater difficulty in transporting through the hydrophobic barrier 160. pH can be controlled by buffering solutes. Therefore, the sample solution 180 and/or sensor solution 140 may contain at least one solute that maintains the analyte in an uncharged state. For example, while Tobramycin can be charged (ionized) in a biological pH range (e.g., 6.8 to 7.2), in some embodiments, the sample solution 180 may be buffered to change the pH outside of a range of 6.8 to 7.2 resulting in an amount of uncharged Tobramycin to be included in the sample solution 180. The uncharged Tobramycin can traverse the hydrophobic barrier 160 for detection by the sensor 120.

With further reference to FIGS. 1A and 1B, hydrophobic barrier 160 could be a solid layer of a polymer, such as a 5 μm thick layer of polymethyldisiloxane (PDMS), which is permeable to certain target analytes, like cortisol. Silicone polymers reconfigure molecularly at a higher rate than other polymers, and therefore are able to transport hydrophilic analytes. However, silicone polymers may still function as a hydrophobic barrier 160 as used herein, so long as the barrier adequately rejects interfering solutes.

With reference to FIG. 1B, the device 100 is placed into contact with a sample solution 180 such as blood, tears, sweat, interstitial fluid, urine, environmental (e.g., river) water, food product solution, or other types of sample solutions. The volume of sample solution 180 could be small, e.g., from a single droplet to an approximately 10 μm thick film, or large, e.g., a cup or more of fluid. Because water and other hydrophilic solvents can still diffuse, albeit slowly, through a hydrophobic barrier, the sensor solution 140 could be contaminated by water or other solvents in the sample solution. In such circumstances, the device sensor 120 would be exposed to sensor solution 140 mixed with water (or other solvent) from the sample solution 180 and some amount of target analyte. In some cases this should be avoided to obtain more accurate measurements of analyte present in the sample solution 180, because increased water or other solvent in the sensor solution 140 could alter pH or salinity or other factors that would interfere with sensor 120 performance. One solution is to regulate the pressure of the sensor solution through applied pressure, osmosis, or other means. For example, the sensor 120 could be an electrochemical aptamer based sensor for measuring cortisol in sweat, and the sensor solution 140 may be a stabilizing solution of at least 1M MgCl with a fixed pH. If the hydrophobic barrier were adequately rigid or supported by a rigid material such as a stainless steel mesh, and the hydrophobic barrier is permeable to both cortisol and water, then even if sample solution 180 has a tenth of the osmolarity of the sensor solution 140, water would not be able to diffuse into sensor solution by osmosis because the volume of sensor solution is physically constrained by the rigid hydrophobic barrier. For example, the rigidity could support pressures such as 15 psi or pressures as high as 100's or 1000's of psi which are generated when the osmolality of the sample solution 180 and sensor solution 140 are different. Similarly, the device could be constructed under a pressurized condition, e.g., two times a standard atmosphere (atm), so that this built-in pressure reduces the amount of water able to enter or leave the sensor solution when the hydrophobic barrier interacts with the sample solution. Therefore, pressure or osmolality for the sensor solution could be at least one of one and a half times, two times, or ten times greater than or less than pressure of the sample solution. Similarly, salinity of the sample solution could be at least one of one and a half times, five times, ten times, or one hundred times greater than or less than a salinity of the sensor solution. Furthermore, a difference in pH of the sample solution and the sensor solution could be at least one of greater than 0.5, greater than 1, greater than 2, or greater than 5 pH units.

With further reference to FIGS. 1A and 1B, in an optical sensing format, sensor 120 could be an optical spectrometer and sample solution 140 could be a molecular beacon aptamer or other optical probe which changes in optical transmission or fluorescence or other optical property in response to binding to a target analyte. Therefore the device 100 may include one or more sensors is an optical sensor and the sensor solution may contains optical probes for sensing the analyte.

Figure 2:
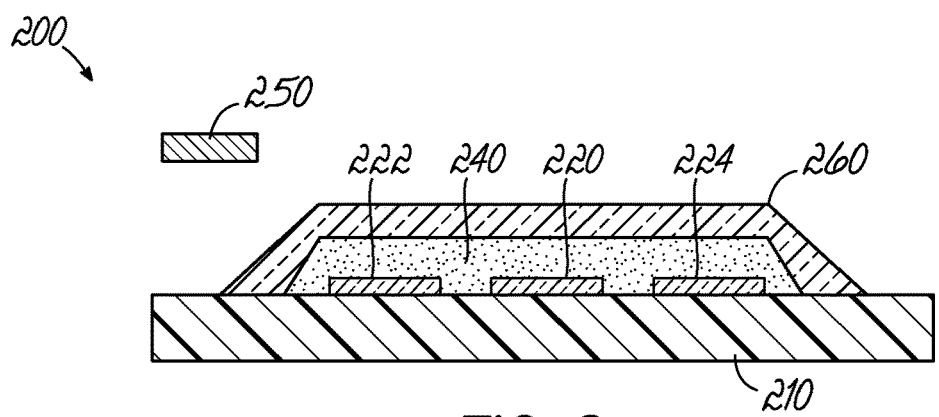
FIG. 2 is cross-sectional view of at least a portion of a sensor of the disclosed invention.

With reference to FIG. 2, where like numerals refer to like features previously described for FIG. 1, the hydrophobic barrier 260 could also be comprised of at least one membrane or other complex of lipid or phospholipid molecules similar to those found in cellular membranes. These lipid or phospholipid molecules or membranes can be arranged in monolayer, double layer, or a plurality of layers. For example, stacked droplets or micelles could comprise the hydrophobic barrier. The described lipid membranes and molecule complexes may be configured to comprise a very thin hydrophobic barrier, which promotes rapid diffusion and high diffusive flux of hydrophobic analytes.

With further reference to FIG. 1B, because of its electrical insulating properties, the hydrophobic barrier 160 could potentially block DC electrical current and hinder sensor 120 operation. Therefore, an electrically insulating hydrophobic barrier material may be configured to promote electrical conductivity, for example, by embedding PDMS with conductive nanoparticles, nanowires, meshes of carbon, metal, or PEDOT, or by embedding other electrically conductive materials. Alternately, if the hydrophobic barrier is too electrically resistive to promote direct charge transfer, charge could be capacitively coupled to the barrier using alternating voltages; that is, the hydrophobic barrier is at least in part an electrical capacitor with one or more electrodes 150 outside the barrier and one or more electrodes (such as a sensor 120) inside the barrier.

With further reference to FIG. 2, the device 200 may include a plurality of sensors or electrodes 220, 222, 224, enclosed by the hydrophobic barrier 260. Since readings by a reference electrode 250 can fluctuate with changing sample solution properties, such as pH or salinity, it may be advantageous to seal a reference sensor and working and counter electrodes (any of sensors 220, 222, 224) inside the hydrophobic barrier. This sensor configuration also eliminates the need for an electrically conductive hydrophobic barrier.

With further reference to FIG. 2, another issue that may arise with the use of a hydrophobic barrier 260 is that a physically thin sensor solution 240 can cause increased electrical resistance to develop between sensor electrodes, degrading sensor function. For example, if two or more sensors 220, 222, 224 have shared electrodes, or electrodes that work together for electrochemical sensing (e.g., working and counter electrodes) and the electrodes are spaced by 1 mm distance, then a physically thin sensor solution of 100 μm thickness would raise electrical resistance between the electrodes and could hamper sensor function. Therefore a plurality of sensor electrodes may be interdigitated, or may be otherwise configured to have a physical distance between their edges that is at least one of less than one hundredth, less than one tenth, or less than the same amount of the physical distance between the hydrophobic barrier and the electrodes.

With further reference to FIGS. 1 and 2, a hydrophobic barrier 160, 260 as described presents concrete advantages for sensor function in electrically noisy biofluids. For example, for electrochemical enzymatic sensors and aptamer sensors, impedimetric sensors, and other sensors, when placed in biofluid samples of interest, such as sweat, blood, interstitial fluid, or saliva, contain a large amount of untargeted solutes that are redox active, the redox active solutes increase the background electrical current or noise. Fortunately, the majority of these untargeted solutes are charged or hydrophilic so that they are unable to diffuse through a hydrophobic barrier, thereby decreasing the background electrical current for a sensor 220 in the sensor solution 240 by at least two times, five time, ten times, one hundred times, or one thousand times, compared to background electrical noise in the sample solution 280. Additionally, degradation from proteases and DNAses can impact the robustness of the sensor, and may also be blocked by the hydrophobic barrier 160, 260.

With further reference to FIG. 1, if the hydrophobic barrier 160 is oil-based or another material that could foul or damage the sensor 120, some embodiments of the disclosed device may further comprise a hydrophilic coating 140, such as sucrose or a collagen hydrogel, to protect the sensor 120 from fouling by the hydrophobic barrier during use or fabrication. In other embodiments, the sensor 120 may also include a spacer, e.g., a plurality of patterned pillars of SU-8 photo-definable epoxy, that separate the hydrophobic barrier from the sensor surface to prevent contact between the sensor and hydrophobic materials. The disclosed invention may therefore include one or more hydrophilic coatings or spacers between the hydrophobic barrier and the sensor.

Figure 3:
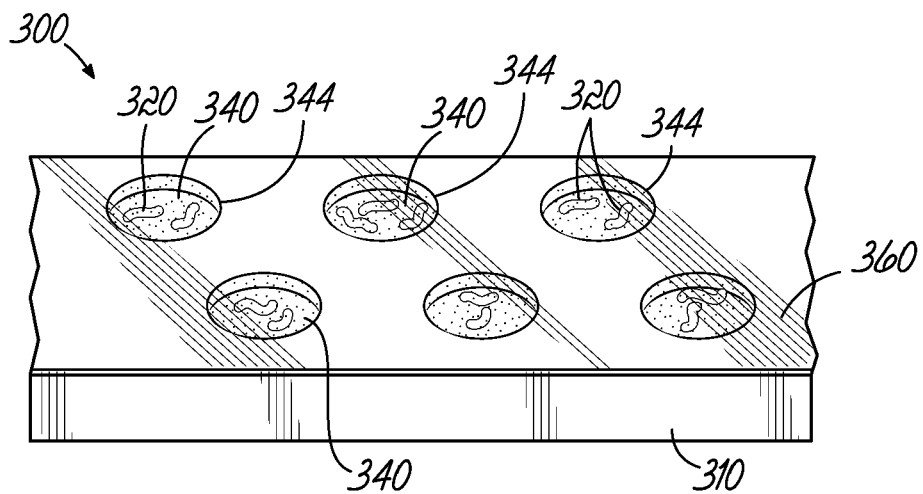
FIG. 3 is cross-sectional view of at least a portion of a fully encapsulated sensor of the disclosed invention.

With reference to FIG. 3, where like numerals refer to like features previously described, a device 300 has solvent, solution, or fluid 340 and sensor or sensing material 320 that is fully enclosed by a hydrophobic barrier 360 forming at least one enclosed volume 344. For example, the sensing material is an optical aptamer probe for testosterone, and the solvent 340 is an aqueous solution. When the device is exposed to a sample as previously taught for FIGS. 1 and 2, testosterone from the sample diffuses through the hydrophobic barrier to the solvent and sensing material. Binding of testosterone to the sensing material causes a change in the optical transmission wavelength (colorimetric) or optical fluorescence (fluorometric) of the sensor. In such embodiments, the sensor could be a molecular beacon-based aptamer sensor where a bound tag and quencher are added to the aptamer (fluorometric). In other cases, the sensing material is based on aptamers and gold nanoparticles (colorimetric). Further, these embodiments also encapsulate the sensor and solvent in a hydrophobic barrier that reduces or prevents diffusion of ions or other charged or hydrophilic species. Therefore, such embodiments benefit from the same advantages described previously for membrane-enhanced sensors, namely improved responsiveness to target analyte concentrations, with less sensitivity to pH or salinity fluctuations, or other confounding factors.

The device 300 can be fabricated simply by starting with a liquid precursor to the hydrophobic barrier, adding an emulsifier or surfactant to the precursor material, and then blending the precursor material with solvent and sensing material so that droplets of solvent and sensing material 344 are suspended in a solid hydrophobic barrier. Transforming a liquid precursor into a hydrophobic barrier as described may be performed by drying, cross-linking, melting then solidifying, or other known means of forming a solid material from a liquid, such as the process used to fabricate polymer-dispersed liquid crystal films. Using such methods the device 300 could include a simple 'paint-on' sensor that is stable in a sample solution with varying pH and salinity.

Because exposure to ultraviolet light can damage or degrade sensor function, the device could further comprise a UV-absorbing coating, e.g., Kapton (not shown), or the hydrophobic barrier could include a UV absorbing material or other suitable materials or methods that prevent UV light from reaching the sensing material.

Figure 4:
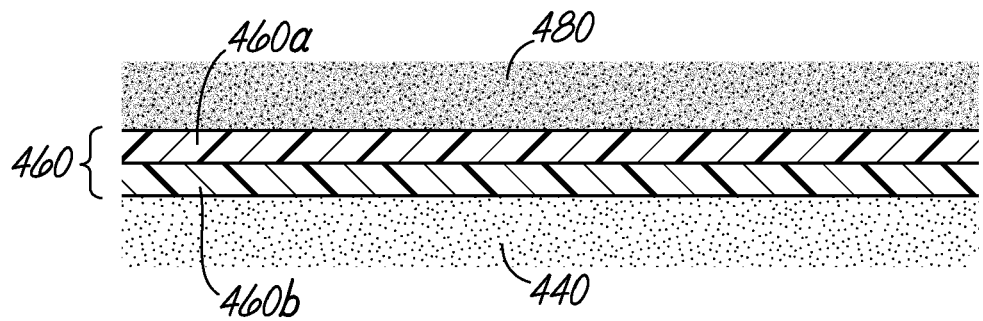
FIG. 4 is cross-sectional view of at least a portion of the hydrophobic barrier of a sensor of the disclosed invention.

With reference to FIG. 4, where like numerals refer to like features previously described, a hydrophobic barrier 460 could be comprised of a first layer 460a, such as a silicone polymer, and a second layer 460b, such as a track etch membrane with a volatile oil. The polymer layer 460a inhibits or prevents evaporation of the volatile oil layer 460b, while the volatile oil layer 460b functions to block hydrophilic solutes from interacting with the sensor. Therefore, the hydrophobic barrier 460 may include a plurality of layers, for example layers 460a, 460b, and among the plurality of layers are alternating layers of one or more solid materials and one or more fluid materials.

Figure 5:
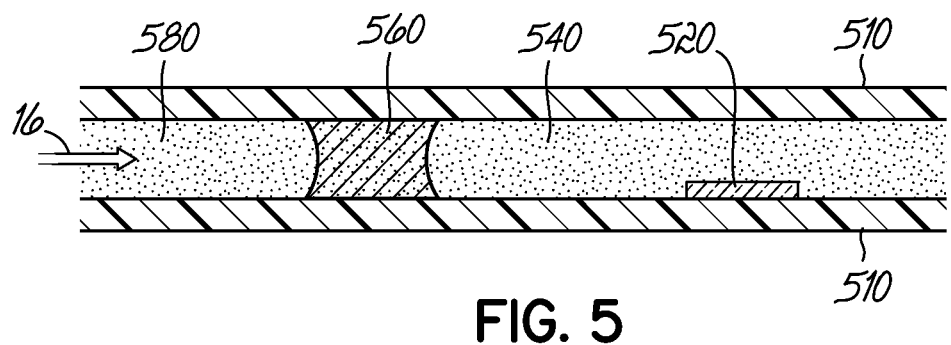
FIG. 5 is a cross-sectional view of at least a portion of a sensor of the disclosed invention.

With reference to FIG. 5, where like numerals refer to like features previously described, a simplified embodiment is depicted to illustrate that membrane enhanced sensor devices as described herein are not limited to the specific designs shown above, and that the invention broadly includes the performance and function characteristics of a hydrophobic barrier. In this simplified device 500, a glass capillary tube 510 is 0.5 mm in diameter and contains a sensor 520. Upstream of the sensor, as indicated by the direction of the arrow 16, the hydrophobic barrier 560 includes a single plug of castor oil that is 1 mm long, and spans the diameter of the capillary tube, so that target analytes in the sample solution must cross the hydrophobic barrier to reach the sensor. Such a simple device would include the function of a hydrophobic barrier as described herein.

Example 1

Enzymes are most commonly deployed as real-time sensors in vivo, as they convert target substrates into byproducts, while also creating a change in the oxidation state of the cofactor (typically nicotinamide adenine dinucleotide, nicotinamide adenine dinucleotide phosphate, or Flavin adenine dinucleotide. Generation of these compounds is either measured directly using amperometry or coulometry via electrochemical oxidation/reduction or indirectly through redox mediators that transfer electrons/oxidation states from the co-factor closer to the electrodes. Typical mediators deployed include Prussian blue, ferrocene, methylene blue, or others that are immobilized on the working electrode of a traditional 3-electrode set-up.

Advances in molecular biology have now made available commercially or via recombinant protein expression soluble enzymes for difficult to measure hydrophobic analytes, including enzymes for cortisol (11 beta-hydroxysteroid dehydrogenase) and testosterone (testosterone 17beta-dehydrogenase). The relative instability and cost of these enzymes in conjunction with the low concentrations of the analytes the enzymes are detecting (micromolar to nanomolar) requires sequestration of the enzymes behind a hydrophobic barrier in order to remove interfering solutes such as charged interfering redox active compounds (micromolar concentrations). Additionally, because these enzymes operate reversibly, additional steps must be taken to amplify signals for detection in many instances.

Amplification of a signal can be obtained behind the membrane in multiple ways, such as: 1) as cortisol continues to be converted to cortisone, the analyte concentration of cortisol will decrease and cortisone to increase, causing a continued influx of cortisol, efflux of byproduct cortisone, thus shifting the equilibrium concentrations, and continuing generation of the reduced byproduct (NADH or NADPH). The NADH/NADPH (due to its −2 charge) remains trapped behind the hydrophobic barrier until electrochemical oxidation to reform NAD+/NADP+ through application of a reductive potential; the time delay between pulses can be changed to trade sensitivity of measurement for time resolution of measurement.

Hydrophobic barriers of the present invention will also reduce background current due to oxidation or reduction reactions involving solutes in the sample solution, because fewer of those solutes will reach the sensor surfaces. Having reduced background signal improves the sensor's limit of detection as well as the reproducibility of the measurements. For example, the invention could enable an ultra-low limit of detection enzymatic ethanol sensor for fuel exposure, or could allow enzymatic cortisol concentration measurements via detecting the byproducts of enzymatic cortisol reactions. Cortisol is metabolized by the 11-beta hydroxysteroid dehydrogenase system (11-beta HSD), which includes of two enzymes: 11-beta HSD1 and 11-beta HSD2. 11-beta HSD1 uses the cofactor NADPH to convert biologically inert cortisone to biologically active cortisol. 11-beta HSD2 uses the cofactor NAD+ to convert cortisol to cortisone. Overall, the net effect is that 11-beta HSD1 and 11-beta HSD2 serve to increase and decrease, respectively, the local concentration of biologically active cortisol in a given tissue. Cortisol is also metabolized into 5-alpha tetrahydrocortisol (5-alpha THF) and 5-beta tetrahydrocortisol (5-beta THF), reactions for which 5-alpha reductase and 5-beta reductase are the rate-limiting factors, respectively. 5-Beta reductase is also the rate-limiting factor in the conversion of cortisone to tetrahydrocortisone, Example 2

Figure 6A:
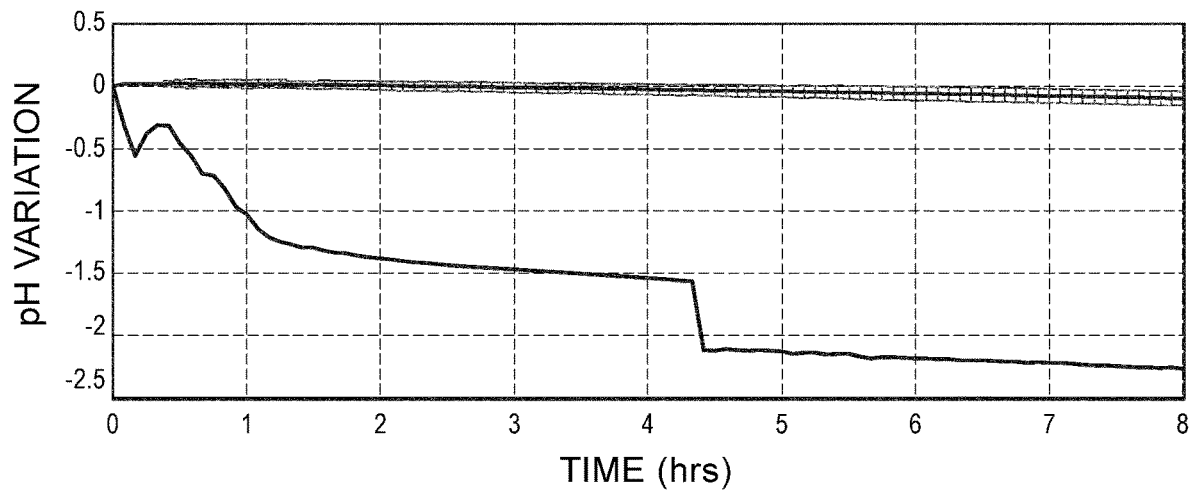
FIG. 6A depicts potential of hydrogen (pH) variation over time for a sensor of the disclosed invention.

Electrochemical aptamer sensors are often reversible sensors with low limits of detection for target analytes. However, electrochemical apatamer sensors can be sensitive to changes in solutes such as pH and salinity, are sensitive to redox active solutes in the sample, and are readily degraded by other solutes in raw biofluids. The majority of the interfering solutes are hydrophilic, and can be kept separate from the sensor by use of the hydrophobic membrane as taught herein. An electrochemical aptamer sensor for cortisol was fabricated on gold electrodes, and sealed with a sensor solution of 50 mM NaCl and pH of 6.5. Several tests were then performed to test the effectiveness of the hydrophobic barrier. First, the pH behind the hydrophobic barrier (against the sensor) was tested over multiple hours as shown in FIG. 6A. In this example, a hydrophobic track-etch membrane was filled with Castor oil in its pores, and the membrane epoxied with a spacer ring onto the sensor. In FIG. 6A, the sensor was a simple pH electrode with a sensor solution pH of 6.5. The top plots shown in FIG. 6A are with the castor oil, showing almost no pH variation over a long period of hours even as the device was placed in an acid solution. The bottom plot in FIG. 6A was the same device construction, but no castor oil was used in the track etch membrane, such that a hydrophobic barrier was not created, and as expected the pH decreased over time.

Figure 6B:
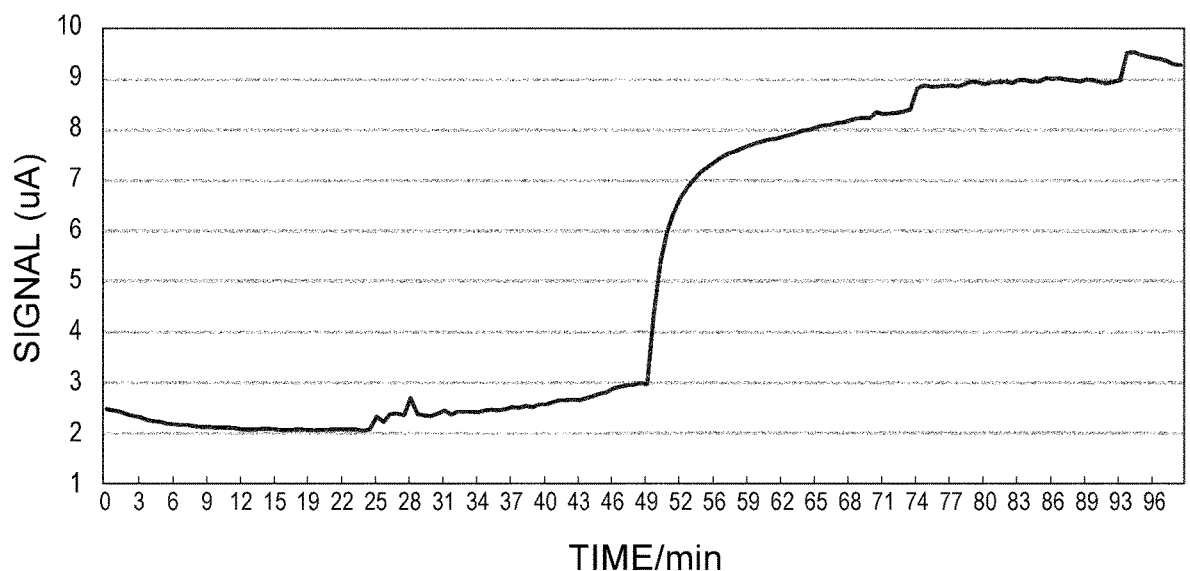
FIG. 6B depicts signal change over time of a sensor of the disclosed invention.

In FIG. 6B, a similar setup was used where the following tests were performed. The sensor was the electrochemical aptamer sensor for cortisol, protected by a hydrophobic barrier having a track etch membrane with castor oil in the membrane's pores. The sensor solution was pH 6.5 and 50 mM NaCl. At t=0 minutes the sensor was then placed in a solution of pH 6.5 and no cortisol, at t=24 minutes the sensor was then placed in a solution of pH 3 and no cortisol, at t=48 minute the sensor was placed in a solution of pH 6.5 and 10 µM cortisol. The experiment was also repeated (not shown) at similar 24 minute intervals, and the pH and cortisol levels were changed again, including pH 3 and 10 µM cortisol, and the sensor responded only to changes in cortisol concentrations and not to pH. This test shows the sensor operating reliably even though the sample solution pH changed over levels that would degrade or interfere with the sensor. Simply, the hydrophobic barrier was porous to the target analyte (cortisol) and non-porous to interfering solutes such as pH.

What is claimed is:

1. A sensing device, comprising:
   one or more sensors configured to measure a characteristic of an analyte in a sample;
   a sample solution that contains the analyte and one or more interfering solutes, wherein the interfering solute reduces a performance characteristic of the one or more sensors;
   a sensor solution in fluidic communication with the one or more sensors; and
   a hydrophobic barrier that separates the sample solution from the one or more sensors, wherein the hydrophobic barrier is permeable to the analyte and impermeable to the interfering solute, and wherein the hydrophobic barrier is in fluidic communication with the sample solution and the sensor solution; and
   wherein the one or more sensors is an electrochemical aptamer sensor with an attached redox couple.

2. The device of claim 1, wherein the one or more sensors is at least one of the following: a continuous sensor, and a reversible sensor.

3. The device of claim 1, wherein the analyte is at least one of the following: a steroid hormone, a drug, or a peptide.

4. The device of claim 1, wherein the sample solution contains at least one of the following: a salt, a buffering solute, or a preservative.

5. The device of claim 1, wherein the hydrophobic barrier is at least partially comprised of a fluid supported by a solid scaffold.

6. The device of claim 1, wherein the hydrophobic barrier has a thickness that is at least one of less than 1 millimeter, less than 100 micrometers, less than 10 micrometers, less than 1 micrometer, or less than 0.1 micrometers.

7. The device of claim 1, wherein the hydrophobic barrier has a porosity that is at least one of greater than 0.1%, greater than 1%, greater than 10%, or greater than 30%.

8. The device of claim 1, further comprising an interior space at least partially defined by the hydrophobic barrier, wherein the sensor solution is disposed in the interior space, and wherein the interior space has a thickness in at least one direction that is at least one of less than 3 millimeters, less than 1 millimeter, less than 300 micrometers, less than 100 micrometers, less than 30 micrometers, or less than 10 micrometers.

9. The device of claim 1, further comprising a concentration lag time that is at least one of less than 300 minutes, less than 100 minutes, less than 30 minutes, less than 10 minutes, less than 3 minutes, or less than 1 minute.

10. The device of claim 1, wherein the hydrophobic barrier is comprised of at least one solute.

11. The device of claim 1, wherein the sample solution is further comprised of at least one solute that maintains the analyte in an uncharged state.

12. The device of claim 1, wherein the sensor solution is further comprised of at least one solute that maintains the analyte in an uncharged state.

13. The device of claim 1, wherein the hydrophobic barrier is a solid polymer.

14. The device of claim 1, wherein the hydrophobic barrier is at least one of the following; comprised of a rigid material, or supported by a rigid material.

15. The device of claim 14, wherein the sensor solution is physically constrained in its volume by the hydrophobic barrier.

16. The device of claim 1, wherein a pressure of the sensor solution is at least one of one and a half times, two times, or ten times greater than or less than a pressure of the sample solution.

17. The device of claim 1, wherein a salinity of the sample solution is at least one of one and a half times, five times, ten times, or one hundred times greater than or less than a salinity of the sensor solution.

18. The device of claim 1, wherein the hydrophobic barrier is comprised of at least one of the following: a monolayer of molecules, a double layer of molecules, a plurality of monolayers, or a plurality of double layers.

19. The device of claim 1, wherein the hydrophobic barrier is electrically conducting.

20. The device of claim 1, wherein each of the one or more sensors is comprised of a plurality of electrodes.

21. The device of claim 20, wherein at least two of the plurality of electrodes have a physical distance between their edges that is at least one of less than one hundredth, less than one tenth, or less than a same amount of the physical distance between the hydrophobic barrier and the at least two electrodes.

22. The device of claim 1, further comprising a first background current and a second background current, wherein the first background current is present in the sample solution, the second background current is present in the sensor solution, and wherein the second background current is less than the first background current by at least one of two times, five time, ten times, one hundred times, or one thousand times.

23. The device of claim 1, wherein the sample solution is a biofluid.

24. The device of claim 23, wherein the biofluid is sweat.

25. The device of claim 1, wherein the one or more sensors is an optical sensor and the sensor solution contains optical probes for sensing the analyte.

26. A sensing device, comprising:
one or more sensors configured to measure a characteristic of an analyte in a sample;
a sample solution that contains the analyte and one or more interfering solutes, wherein the interfering solute reduces a performance characteristic of the one or more sensors;
a sensor solution in fluidic communication with the one or more sensors;
a hydrophobic barrier that separates the sample solution from the one or more sensors, wherein the hydrophobic barrier is permeable to the analyte and impermeable to the interfering solute, and wherein the hydrophobic barrier is in fluidic communication with the sample solution and the sensor solution;
wherein the analyte is at least one of the following: a steroid hormone, a drug, or a peptide.

27. A sensing device, comprising:
one or more sensors configured to measure a characteristic of an analyte in a sample;
a sample solution that contains the analyte and one or more interfering solutes, wherein the interfering solute reduces a performance characteristic of the one or more sensors;
a sensor solution in fluidic communication with the one or more sensors;
a hydrophobic barrier that separates the sample solution from the one or more sensors, wherein the hydrophobic barrier is permeable to the analyte and impermeable to the interfering solute, and wherein the hydrophobic barrier is in fluidic communication with the sample solution and the sensor solution;
wherein the hydrophobic barrier has an octanol and water log10 (Partition Coefficient) (logP) that is at least one of greater than −3, greater than −1, greater than 1, greater than 3, or greater than 5, or wherein the hydrophobic barrier has an analyte logP that is at least one of the following: between −1 and 1, between −3 and 3, or between −5 and 5.

28. A sensing device, comprising:
one or more sensors configured to measure a characteristic of an analyte in a sample;
a sample solution that contains the analyte and one or more interfering solutes, wherein the interfering solute reduces a performance characteristic of the one or more sensors;
a sensor solution in fluidic communication with the one or more sensors;
a hydrophobic barrier that separates the sample solution from the one or more sensors, wherein the hydrophobic barrier is permeable to the analyte and impermeable to the interfering solute, and wherein the hydrophobic barrier is in fluidic communication with the sample solution and the sensor solution;
wherein the hydrophobic barrier is comprised of a fluid with a solubility limit in the sample solution that is at least one of less than 500 micrograms of the fluid per gram of the sample solution, less than 50 micrograms of the fluid per gram of sample solution, less than 5 micrograms of the fluid per gram of the sample solution, or less than 0.5 micrograms of the fluid per gram of the sample solution.

29. The sensing device of claim 28, wherein the hydrophobic barrier has an operating lifetime of at least one of greater than 3 hours, greater than 30 hours, greater than 300 hours, or greater than 3000 hours.

30. A sensing device, comprising:
one or more sensors configured to measure a characteristic of an analyte in a sample;
a sample solution that contains the analyte and one or more interfering solutes, wherein the interfering solute reduces a performance characteristic of the one or more sensors;
a sensor solution in fluidic communication with the one or more sensors;
a hydrophobic barrier that separates the sample solution from the one or more sensors, wherein the hydrophobic barrier is permeable to the analyte and impermeable to the interfering solute, and wherein the hydrophobic barrier is in fluidic communication with the sample solution and the sensor solution;
wherein the hydrophobic barrier is comprised of a plurality of miscible oils or a plurality of immiscible oils.

31. A sensing device, comprising:
one or more sensors configured to measure a characteristic of an analyte in a sample;
a sample solution that contains the analyte and one or more interfering solutes, wherein the interfering solute reduces a performance characteristic of the one or more sensors;
a sensor solution in fluidic communication with the one or more sensors;
a hydrophobic barrier that separates the sample solution from the one or more sensors, wherein the hydrophobic barrier is permeable to the analyte and impermeable to the interfering solute, and wherein the hydrophobic barrier is in fluidic communication with the sample solution and the sensor solution;
wherein the hydrophobic barrier is comprised of at least one surfactant.

32. A sensing device, comprising:
one or more sensors configured to measure a characteristic of an analyte in a sample;
a sample solution that contains the analyte and one or more interfering solutes, wherein the interfering solute reduces a performance characteristic of the one or more sensors;
a sensor solution in fluidic communication with the one or more sensors;
a hydrophobic barrier that separates the sample solution from the one or more sensors, wherein the hydrophobic barrier is permeable to the analyte and impermeable to the interfering solute, and wherein the hydrophobic barrier is in fluidic communication with the sample solution and the sensor solution;
wherein the hydrophobic barrier is comprised of a fluid that at 72 degrees fahrenheit will not evaporate for at least one of greater than 24 hours, greater than 1 week, greater than 1 month, or greater than 1 year.

33. A sensing device, comprising:
one or more sensors configured to measure a characteristic of an analyte in a sample;
a sample solution that contains the analyte and one or more interfering solutes, wherein the interfering solute reduces a performance characteristic of the one or more sensors;
a sensor solution in fluidic communication with the one or more sensors;
a hydrophobic barrier that separates the sample solution from the one or more sensors, wherein the hydrophobic barrier is permeable to the analyte and impermeable to the interfering solute, and wherein the hydrophobic barrier is in fluidic communication with the sample solution and the sensor solution;
wherein the hydrophobic barrier is at least partially comprised of a fluid with a viscosity that is at least one of less than 1000 centipoise, less than 100 centipoise, or less than 10 centipoise.

34. A sensing device, comprising:
one or more sensors configured to measure a characteristic of an analyte in a sample;
a sample solution that contains the analyte and one or more interfering solutes, wherein the interfering solute reduces a performance characteristic of the one or more sensors;
a sensor solution in fluidic communication with the one or more sensors;
a hydrophobic barrier that separates the sample solution from the one or more sensors, wherein the hydrophobic barrier is permeable to the analyte and impermeable to the interfering solute, and wherein the hydrophobic barrier is in fluidic communication with the sample solution and the sensor solution; and
one or more spacers between the one or more sensors and the hydrophobic barrier.

35. A sensing device, comprising:
one or more sensors configured to measure a characteristic of an analyte in a sample;
a sample solution that contains the analyte and one or more interfering solutes, wherein the interfering solute reduces a performance characteristic of the one or more sensors;
a sensor solution in fluidic communication with the one or more sensors;
a hydrophobic barrier that separates the sample solution from the one or more sensors, wherein the hydrophobic barrier is permeable to the analyte and impermeable to the interfering solute, and wherein the hydrophobic barrier is in fluidic communication with the sample solution and the sensor solution;
wherein the hydrophobic barrier is comprised of a plurality of layers, and wherein the plurality of layers is comprised of at least one solid material and at least one fluid material, wherein the solid material and fluid material are deposited in alternating layers.

36. A sensing device, comprising:
one or more sensors configured to measure a characteristic of an analyte in a sample;
a sample solution that contains the analyte and one or more interfering solutes, wherein the interfering solute reduces a performance characteristic of the one or more sensors;
a sensor solution in fluidic communication with the one or more sensors;
a hydrophobic barrier that separates the sample solution from the one or more sensors, wherein the hydrophobic barrier is permeable to the analyte and impermeable to the interfering solute, and wherein the hydrophobic barrier is in fluidic communication with the sample solution and the sensor solution;

wherein the one or more sensors is an enzymatic sensor; and wherein the sensor solution contains a co-factors, and said hydrophobic barrier is impermeable to the co-factor.

* * * * *